US012569455B2

(12) United States Patent  
Izaki et al.

(10) Patent No.: US 12,569,455 B2  
(45) Date of Patent: Mar. 10, 2026

(54) THERAPEUTIC AGENT FOR MYALGIC ENCEPHALOMYELITIS/CHRONIC FATIGUE SYNDROME

(71) Applicant: MITSUBISHI TANABE PHARMA CORPORATION, Osaka (JP)

(72) Inventors: Hitoshi Izaki, Osaka (JP); Rikako Hayashi, Osaka (JP); Yoshiari Yanai, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 826 days.

(21) Appl. No.: 17/795,609

(22) PCT Filed: Feb. 5, 2021

(86) PCT No.: PCT/JP2021/004216  
§ 371 (c)(1),  
(2) Date: Jul. 27, 2022

(87) PCT Pub. No.: WO2021/157682  
PCT Pub. Date: Aug. 12, 2021

(65) Prior Publication Data  
US 2023/0055568 A1      Feb. 23, 2023

(30) Foreign Application Priority Data  
Feb. 6, 2020      (JP) ................................. 2020-019153

(51) Int. Cl.  
*A61K 31/137* (2006.01)  
*A61P 21/00* (2006.01)  
*A61P 25/00* (2006.01)  
*A61P 43/00* (2006.01)

(52) U.S. Cl.  
CPC ............ *A61K 31/137* (2013.01); *A61P 43/00* (2018.01)

(58) Field of Classification Search  
CPC ......... A61K 31/137; A61P 21/00; A61P 25/00  
See application file for complete search history.

(56) References Cited

U.S. PATENT DOCUMENTS

2009/0029947 A1      1/2009 Wallace et al.  
2009/0137530 A1      5/2009 Kiuchi et al.

FOREIGN PATENT DOCUMENTS

| CN | 101674819 A | | 3/2010 |
|----|-------------|---|--------|
| EP | 2805730 | * | 5/2013 |
| WO | WO 2007/069712 A1 | | 6/2007 |
| WO | WO 2008/135522 A1 | | 11/2008 |

OTHER PUBLICATIONS

Morris G, Maes M. Myalgic encephalomyelitis/chronic fatigue syndrome and encephalomyelitis disseminata/multiple sclerosis show remarkable levels of similarity in phenomenology and neuroimmune characteristics. BMC Med. Sep. 17, 2013;11:205.*  
Extended European Search Report for European Application No. 24213294.2, dated Feb. 5, 2025.  
Thieme et al., "Evidenced-Based Guidelines on the Treatment of Fibromyalgia Patients: Are They Consistent and If Not, Why Not? Have Effective Psychological Treatments Been Overlooked?", The Journal of Pain, vol. 18, No. 7, Dec. 27, 2016, XP085092201, pp. 747-756.  
Sotzny et al., "Myalgic Encephalomyelitis/Chronic Fatigue Syndrome—Evidence for an autoimmune disease," Autoimmunity Reviews, vol. 17, 2018, pp. 601-609.  
International Search Report dated Apr. 6, 2021 for Application No. PCT/JP2021/004216 with an English translation.  
Kataoka et al., "MT-1303, a novel sphingosine 1 phosphate (SIP) receptor modulator, ameliorates experimental autoimmune encephalomyelitis (EAE) In mice", Multiple Sclerosis Journal, vol. 21, No. S11, 2015, p. 686.  
Maes et al., "Evidence for Inflammation and activation of cell-mediated immunity in Myalgic Encephalomyelitis/Chronic Fatigue Syndrome (ME/CFS): . . . neopterin", Journal of Affective Disorders, vol. 136, 2012 (Available online Oct. 4, 2011), pp. 933-939.  
Nakatomi et al., "Neuroinflammation in Patients with Chronic Fatigue Syndrome/Myalgic Encephalomyelitis: An 11C-(R)-PK11195 PET Study", J Nucl Med, vol. 55, No. 6, 2014 (Published online Mar. 24, 2014), pp. 945-950.  
Li, "Functional Medicine," Anhui Science and Technology Press, Mar. 2014, p. 246, with partial English translation (3 pages total).  
Shimano et al., "Amiselimod (MT-1303), a novel sphingosine 1-phosphate receptor-1 functional antagonist, inhibits progress of chronic colitis induced by transfer of CD4+CD45RBhigh T cells," PLoS One, vol. 14, No. 12, e0226154, Dec. 5, 2019, pp. 1-12.  
Yan, "Handbook for Diagnosis and Treatment of Common Rheumatology," China Medical Science and Technology Press, Jun. 2011, p. 210, with partial English translation (3 pages total).

*Primary Examiner* — Sahar Javanmard  
(74) *Attorney, Agent, or Firm* — Birch, Stewart, Kolasch & Birch, LLP

(57) ABSTRACT

The present invention aims to provide a therapeutic agent for myalgic encephalomyelitis/chronic fatigue syndrome (ME/CFS) and fibromyalgia. A therapeutic agent for a disease selected from myalgic encephalomyelitis/chronic fatigue syndrome, and fibromyalgia, containing 2-amino-2-[2-(4-heptyloxy-3-trifluoromethylphenyl)ethyl]propane-1,3-diol or a pharmaceutically acceptable salt thereof.

13 Claims, 1 Drawing Sheet

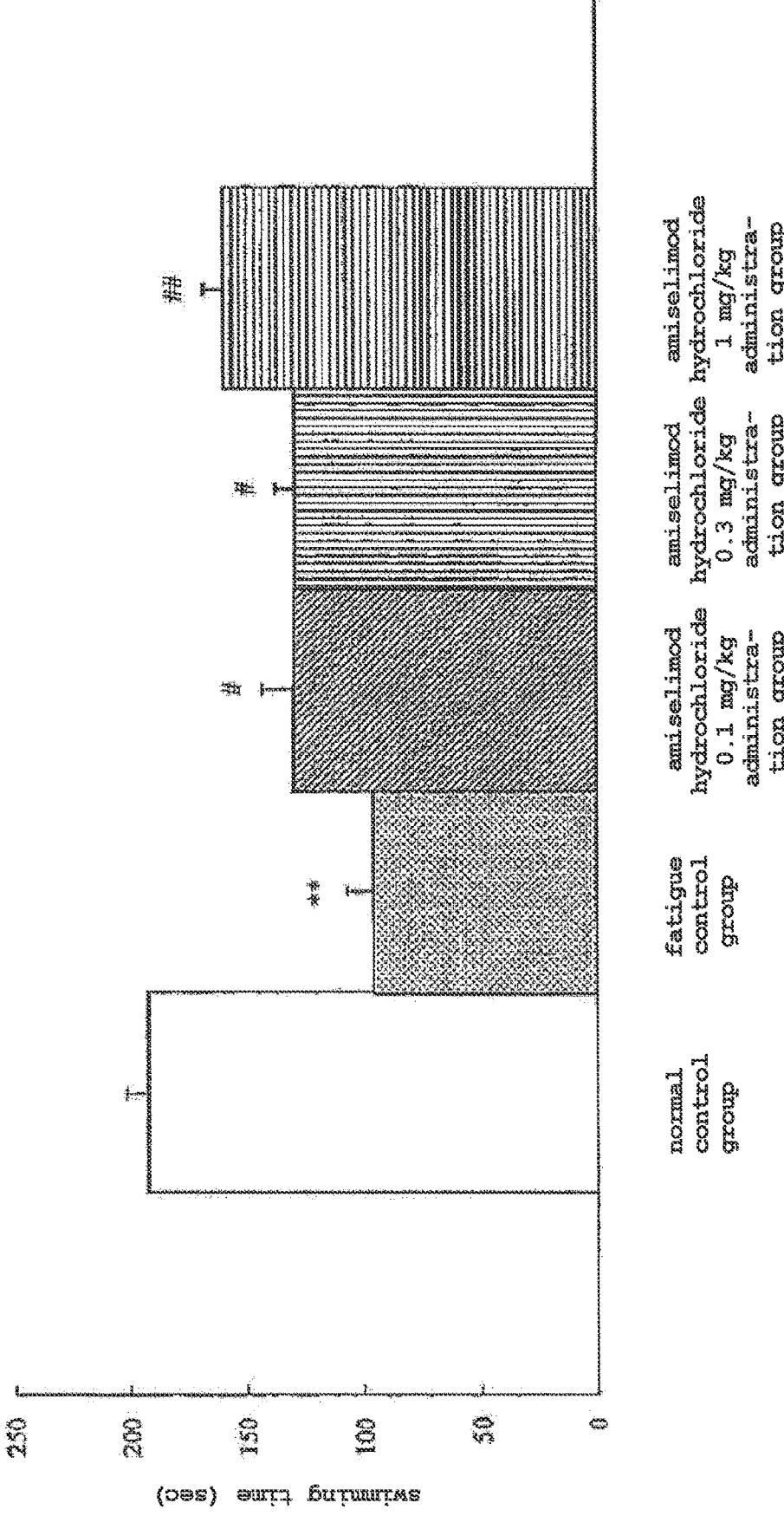

THERAPEUTIC AGENT FOR MYALGIC ENCEPHALOMYELITIS/CHRONIC FATIGUE SYNDROME

TECHNICAL FIELD

The present invention relates to a therapeutic agent for myalgic encephalomyelitis (ME)/chronic fatigue syndrome (CFS), and fibromyalgia.

BACKGROUND ART

Myalgic encephalomyelitis/chronic fatigue syndrome (ME/CFS) is also referred to as chronic fatigue and immune dysfunction syndrome, SEID (systemic exertion intolerance disease), and the like, and is a disease with the main symptoms of general malaise/fatigue which is so strong that daily life is significantly impaired, slight fever, lymph node swelling, headache, loss of muscle strength, sleep disorder, a decrease in thinking ability and concentration, and the like, under which these conditions do not recover but continue for a long time even after rest. Even with some therapeutic intervention, a certain number of patients are in constant need of assistance in their daily lives due to severe fatigue that debilitates the whole body, weakness, pain in the joint and muscle tendon tissues of the whole body, cognitive dysfunction and the like.

However, there are currently no medicaments approved by the authorities as therapeutic drugs in the United States, Europe or Japan. There are academic reports teaching that some selective serotonin reuptake inhibitors (SSRI), some monoamine oxidation enzymes (MAO) inhibitors and some Chinese herbal medicines alleviate depressive symptoms, pain symptoms, and the like. However, only a small number of cases have been examined or only a part of patients proved effective. Globally, the double-stranded RNA rinta-tolimod. (Ampligen (registered trademark)) received approval only in Argentina.

DOCUMENT LIST

Patent Document

Patent document 1: International Publication NO. WO 2007/069712

SUMMARY OF INVENTION

A method for sufficiently treating myalgic encephalomyelitis/chronic fatigue syndrome (ME/CFS) and fibromyalgia has not been established, and a compound useful for the treatment thereof or a therapeutic agent containing same has been demanded. The present invention aims to provide a therapeutic agent for myalgic encephalomyelitis/chronic fatigue syndrome (ME/CFS) or fibromyalgia.

The present inventors have conducted intensive studies and surprisingly found that 2-amino-2-[2-(4-heptyloxy-3-trifluoromethylphenyl)ethyl]propane-1,3-diol (amiselimod) or a pharmaceutically acceptable salt thereof is useful for myalgic encephalomyelitis/chronic fatigue syndrome (ME/CFS) and fibromyalgia, particularly, for myalgic encephalomyelitis/chronic fatigue syndrome (ME/CFS). They have conducted further studies and completed the present invention.

The present invention provides the following.

[1] A therapeutic agent for a disease selected from myalgic encephalomyelitis/chronic fatigue syndrome (ME/

CFS), and fibromyalgia, comprising 2-amino-2-[2-(4-heptyloxy-3-trifluoromethylphenyl)ethyl]propane-1,3-diol (amiselimod) or a pharmaceutically acceptable salt thereof (e.g., amiselimod hydrochloride).

[2] The therapeutic agent of the above-mentioned [1], wherein the disease is myalgic encephalomyelitis/chronic fatigue syndrome.

[3] The therapeutic agent of the above-mentioned [1] or [2], wherein the myalgic encephalomyelitis/chronic fatigue syndrome is myalgic encephalomyelitis/chronic fatigue syndrome associated with fatigue symptoms.

[4] A method for treating a disease selected from myalgic encephalomyelitis/chronic fatigue syndrome (ME/CFS), and fibromyalgia, comprising administering an effective amount of the therapeutic agent of any of the above-mentioned [1] to [3].

[5] The method of the above-mentioned [4], wherein the disease is myalgic encephalomyelitis/chronic fatigue syndrome.

[6] The method of the above-mentioned [4] or [5], wherein the myalgic encephalomyelitis/chronic fatigue syndrome is myalgic encephalomyelitis/chronic fatigue syndrome associated with fatigue symptoms.

[7] Use of the therapeutic agent of any of the above-mentioned [1] to [3] for treating a disease selected from myalgic encephalomyelitis/chronic fatigue syndrome, and fibromyalgia.

[8] The use of the above-mentioned [7], wherein the disease is myalgic encephalomyelitis/chronic fatigue syndrome.

[9] The use of the above-mentioned [7] or [8], wherein the myalgic encephalomyelitis/chronic fatigue syndrome is myalgic encephalomyelitis/chronic fatigue syndrome associated with fatigue symptoms.

[10] Use of the therapeutic agent of any of the above-mentioned [1] to [3] in producing a therapeutic agent: for a disease selected from myalgic encephalomyelitis/chronic fatigue syndrome, and fibromyalgia.

[11] The use of the above-mentioned [10], wherein the disease is myalgic encephalomyelitis/chronic fatigue syndrome.

[12] The use of the above-mentioned [10] or [11], wherein the myalgic encephalomyelitis/chronic fatigue syndrome is myalgic encephalomyelitis/chronic fatigue syndrome associated with fatigue symptoms.

[13] A therapeutic agent for a disease selected from myalgic encephalomyelitis/chronic fatigue syndrome, and fibromyalgia, comprising 1-[[6-[(2-methoxy-4-propylphenyl)methoxy]-1-methyl-3,4-dihydronaphthalen-2-yl]methyl]azetidine-3-carboxylic acid (ceralifimod), or a pharmaceutically acceptable salt thereof.

[14] A therapeutic agent for a disease selected from myalgic encephalomyelitis/chronic fatigue syndrome, and fibromyalgia, comprising (2S)-3-[4-[5-(2-cyclopentyl-6-methoxypyridin-4-yl)-1,2,4-oxadiazol-3-yl]-2-ethyl-6-methylphenoxy]propane-1,2-diol (cenerimod), or a pharmaceutically acceptable salt thereof.

[15] A therapeutic agent for a disease selected from myalgic encephalomyelitis/chronic fatigue syndrome, and fibromyalgia, comprising 2-[(3R)-7-[[4-cyclopentyl-3-(trifluoromethyl)phenyl]methoxy]-1,2,3,4-tetrahydrocyclopenta[b]indol-3-yl]acetic acid (etrasimod), or a pharmaceutically acceptable salt thereof (e.g., etrasimod arqinine).

[16] A therapeutic agent for a disease selected from myalgic encephalomyelitis/chronic fatigue syndrome, and fibromyalgia, comprising 5-(3-{(1S)-1-[(2-hydroxyethyl)amino]-2,3-dihydro-1H-inden-4-yl}-2-iso-propoxybenzonitrile (ozanimod), or a pharmaceutically acceptable salt thereof (e.g., ozanimod hydrochloride).

[17] A therapeutic agent for a disease selected from myalgic encephalomyelitis/chronic fatigue syndrome, and fibromyalgia, comprising (2Z,5Z)-5-{3-chloro-4-[(2R)-2,3-dihydroxy propoxy]benzylidene}-3-(2-methylphenyl)-2-(propylimino)-1,3-thiazolidin-4-one (ponesimod), or a pharmaceutically acceptable salt thereof.

[18] A therapeutic agent for a disease selected from myalgic encephalomyelitis/chronic fatigue syndrome, and fibromyalgia, comprising 1-(4-[(1E)-N-{[4-cyclo-hexyl-3-(trifluoromethyl)benzyl]oxy}ethaneimidoyl]-2-ethylbenzyl)-3-azetidine carboxylic acid (siponimod), or a pharmaceutically acceptable salt thereof (e.g., siponimod fumarate).

[19] The therapeutic agent of any of the above-mentioned [13] to [18], wherein the disease is myalgic encephalomyelitis/chronic fatigue syndrome.

[20] The therapeutic agent of any of the above-mentioned [13] to [19], wherein the myalgic encephalomyelitis/chronic fatigue syndrome is chronic fatigue syndrome associated with fatigue symptoms.

[21] A method for treating a disease selected from myalgic encephalomyelitis/chronic fatigue syndrome, and fibromyalgia, comprising administering an effective amount of the therapeutic agent of any of the above-mentioned [13] to [20].

[22] The method of the above-mentioned [21], wherein the disease is myalgic encephalomyelitis/chronic fatigue syndrome.

[23] The method of the above-mentioned [21] or [22], wherein the chronic fatigue syndrome is myalgic encephalomyelitis/chronic fatigue syndrome associated with fatigue symptoms.

[24] Use of the therapeutic agent of any of the above-mentioned [13] to [20] for treating a disease selected from myalgic encephalomyelitis/chronic fatigue syndrome, and fibromyalgia.

[25] The use of the above-mentioned [24], wherein the disease is myalgic encephalomyelitis/chronic fatigue syndrome.

[26] The use of the above-mentioned [24] or [25], wherein the chronic fatigue syndrome is myalgic encephalomyelitis/chronic fatigue syndrome associated with fatigue symptoms.

[27] Use of the therapeutic agent of any of the above-mentioned [13] to [20] in producing a therapeutic agent for a disease selected from myalgic encephalomyelitis/chronic fatigue syndrome (ME/CFS), and fibromyalgia.

[28] The use of the above-mentioned [27], wherein the disease is myalgic encephalomyelitis/chronic fatigue syndrome.

[29] The use of the above-mentioned [27] or [28], wherein the chronic fatigue syndrome is myalgic encephalomyelitis/chronic fatigue syndrome associated with fatigue symptoms.

According to the present invention, a novel therapeutic agent for myalgic encephalomyelitis/chronic fatigue syndrome (ME/CFS), and a novel therapeutic agent for fibromyalgia can be provided.

BRIEF DESCRIPTION OF DRAWINGS

FIG. 1 shows the effectiveness of amiselimod hydrochloride on swimming time in a weight-loaded forced swimming test of an animal model (fatigue rat) with myalgic encephalomyelitis/chronic fatigue syndrome (ME/CFS). A significant difference was observed in the fatigue control group as compared with the normal control group (in FIG. 1, **: $p < 0.01$, according to Student's t-test). A significant difference was observed in the amiselimod hydrochloride 0.1 mg/kg administration group, amiselimod hydrochloride 0.3 mg/kg administration group, and amiselimod hydrochloride 1 mg/kg administration group as compared with the fatigue control group (in FIG. 1, #: $p < 0.05$, ##: $p < 0.01$, according to Williams multiple comparison test).

DESCRIPTION OF EMBODIMENTS

Preferred embodiments of the present invention are shown below.

The therapeutic agent in the present invention is specifically a therapeutic agent containing a compound selected from 2-amino-2-[2-(4-heptyloxy-3-trifluoromethylphenyl) ethyl]propane-1,3-diol (amiselimod), 1-[[6-[(2-methoxy-4-propylphenyl)methoxy]-1-methyl-3,4-dihydronaphthalen-2-yl]methyl]azetidine-3-carboxylic acid (ceralifimod), (2S)-3-[4-[5-(2-cyclopentyl-6-methoxypyridin-4-yl)-1,2,4-oxadiazol-3-yl]-2-ethyl-6-methylphenoxy]propane-1,2-diol (cenerimod), 2-[(3R)-7-[[4-cyclopentyl-3-(trifluoromethyl) phenyl]methoxy]-1,2,3,4-tetrahydrocyclopenta[b]indol-3-yl]acetic acid (etrasimod), 5-(3-{(1S)-1-[(2-hydroxyethyl) amino]-2,3-dihydro-1H-inden-4-yl}-2-isopropoxybenzonitrile (ozanimod), (2Z,5Z)-5-{3-chloro-4-[(2R)-2,3-dihydroxy propoxy]benzylidene}-3-(2-methylphenyl)-2-(propylimino)-1,3-thiazolidin-4-one (ponesimod), and 1-{4-[(1E)-N-{[4-cyclohexyl-3-(trifluoromethyl)benzyl]oxy}ethaneimidoyl]-2-ethylbenzyl}-3-azetidinecarboxylic acid (siponimod) or a pharmaceutically acceptable salt thereof (sometimes to be collectively referred to as the active ingredient in the present specification), preferably a therapeutic agent containing 2-amino-2-[2-(4-heptyloxy-3-trifluoromethylphenyl)ethyl]propane-1,3-diol (amiselimod) or a pharmaceutically acceptable salt thereof, particularly preferably a therapeutic agent containing 2-amino-2-[2-(4-heptyloxy-3-trifluoromethylphenyl)ethyl] propane-1,3-diol hydrochloride (amiselimod hydrochloride).

In one embodiment, the therapeutic agent is preferably a therapeutic agent containing a compound selected from amiselimod hydrochloride, ceralifimcd, cenerimod, etrasimod arginine, ozanimod hydrochloride, ponesimod and siponimod fumarate, more preferably a therapeutic agent containing amiselimod hydrochloride.

In the present invention, the compound used as the active ingredient or a pharmaceutically acceptable salt thereof can be produced, for example, by the following production method, and it may be produced by any known method.

Amiselimod or a pharmaceutically acceptable salt thereof can be produced, for example, by the method described in patent document 1.

Ceralifimod or a pharmaceutically acceptable salt thereof can be produced, for example, by the method described in International Publication No. WO 2005/020882.

Cenerimod or a pharmaceutically acceptable salt thereof can be produced, for example, by the method described in International Publication No. WO 2011/007324.

Etrasimod or a pharmaceutically acceptable salt thereof can be produced, for example, by the method described in International Publication No. WO 2010/011316.

Ozanimod or a pharmaceutically acceptable salt thereof can be produced, for example, by the method described in International Publication No. WO 2011/060389.

Ponesimod or a pharmaceutically acceptable salt thereof can be produced, for example, by the method described in International Publication No. WO 2005/054215.

Siponimod or a pharmaceutically acceptable salt thereof can be produced, for example, by the method described in International Publication No. WO 2004/103306.

Examples of the pharmaceutically acceptable salt in the present invention include inorganic acid salt, organic acid salt, alkali metal salt, alkaline earth metal salt, and the like.

The therapeutic agent for a disease selected from myalgic encephalomyelitis/chronic fatigue syndrome and fibromyalgia in the present invention is preferably a therapeutic agent for myalgic encephalomyelitis/chronic fatigue syndrome, more preferably a therapeutic agent for myalgic encephalomyelitis/chronic fatigue syndrome associated with fatigue symptoms.

In one embodiment, the therapeutic agent for a disease selected from myalgic encephalomyelitis/chronic fatigue syndrome and fibromyalgia in the present invention can also be used as a prophylactic agent for a disease selected from myalgic encephalomyelitis/chronic fatigue syndrome and fibromyalgia.

The prophylactic agent for a disease selected from myalgic encephalomyelitis/chronic fatigue syndrome and fibromyalgia is preferably a prophylactic agent for myalgic encephalomyelitis/chronic fatigue syndrome, more preferably a prophylactic agent for myalgic encephalomyelitis/chronic fatigue syndrome associated with fatigue symptoms.

In the present specification, the fatigue symptoms refer to, for example, symptoms that last or recur repeatedly (observed in 50% or more of the evaluation period used for diagnosis) for at least 6 months in which the main symptom is strong fatigue that significantly impairs daily life, preferably, symptoms that last or recur repeatedly for at least 6 months in which the main symptom is as mentioned above and general malaise after a light labor lasts for 24 hours or more and is not relieved by rest or sleep.

In the present invention, examples of the "fatigue symptoms" of the "myalgic encephalomyelitis/chronic fatigue syndrome associated with fatigue symptoms" include fatigue symptoms satisfying the following (a); preferably fatigue symptoms satisfying the following (a) and (b); more preferably fatigue symptoms satisfying the following (a), (b) and (c); particularly preferably fatigue symptoms satisfying the following (a), (b) and (c), and (d) and/or (e).

(a) Significant hypofunction or dysfunction is observed compared to the occupational, academic, social, and personal activity levels before the onset, and lasts for 6 months or more accompanied by a feeling of fatigue. The level thereof is often severe to the extent that it is equivalent to apparent onset of the disease, and the symptoms are not caused by recent excessive labor and are not alleviated by rest.

(b) malaise after labor (c) no recovery by sleeping (d) disorder of cognition function (e) unable to get up or stand As the therapeutic agent of the present invention, the active ingredient may be administered as it is to a patient. Preferably, it is administered as a preparation in the form of a pharmaceutical composition containing the active ingredient and a pharmaceutically acceptable additive.

Examples of the pharmaceutically acceptable additive include excipient, disintegrant, disintegration aid, binder, lubricant, coating agent, dye, diluent, base, dissolving agent, solubilizing agent, isotonicity agent, pH adjuster, stabilizer, propellant, adhesive, and the like.

Examples of the preparation suitable for oral administration include tablet, capsule, powder, fine granules, granule, liquid, syrup and the like, and examples of the preparation suitable for parenteral administration include injection, drip infusion, suppository, and the like.

In the preparation suitable for oral administration, for example, excipients such as glucose, lactose, D-mannitol, starch, crystalline cellulose, and the like; disintegrants or disintegration aid such as carboxymethylcellulose, starch, carboxymethylcellulose calcium, and the like; binders such as hydroxypropylcellulose, hydroxypropylmethylcellulose, polyvinylpyrrolidone, gelatin, and the like; lubricants such as magnesium stearate, talc and the like; coating agents such as hydroxypropylmethylcellulose, sucrose, polyethylene glycol, titanium oxide, and the like; bases such as petrolatum, liquid paraffin, polyethylene glycol, gelatin, kaolin, glycerol, purified water, hard fat, and the like can be used as additives. In the preparation suitable for injection or drip, dissolving agents or solubilizing agents that can constitute an aqueous or on-use soluble injection such as injectable distilled water, saline, propylene glycol, and the like; isotonicity agents such as glucose, sodium chloride, D-mannitol, glycerol, and the like; pH adjusters such as inorganic acid, organic acid, inorganic base, organic base, and the like; and the like can be used as preparation additives.

The administration route of the therapeutic agent of the present invention is not particularly limited, and the therapeutic agent can be administered orally or parenterally (e.g., intravenous, intramuscular, subcutaneous or intradermal injection, drip, or inhalation, and the like), preferably orally.

The dose of the therapeutic agent of the present invention can be appropriately determined according to various conditions such as the kind of the disease to be the treatment target, progression of disease or degree of symptoms, age and body weight of patients, and the like.

The daily dose of amiselimod for an adult is, for example, 0.05 mg-1.0 mg, preferably, 0.08 mg-0.7 mg, more preferably, 0.1 mg-0.4 mg, for example, as amiselimod hydrochloride.

The daily dose of ceralifimod for an adult is, for example, 0.05-0.3 mg, preferably, 0.05-0.15 mg, more preferably, 0.05 mg, 0.10 mg, or 0.15 mg.

The daily dose of cenerimod for an adult is, for example, 0.5-25 mg, preferably, 0.5-4 mg, more preferably, 0.5, 1, 2, or 4 mg.

The daily dose of etrasimod for an adult is, for example, etrasimod arginine, for example, 1-2 mg, preferably, 1 mg, or 2 mg.

The daily dose of ozanimod for an adult is, for example, 0.25-2 mg, preferably, 0.5 mg, or 1 mg, for example, as ozanimod hydrochloride, The daily dose of ponesimod for an adult is, for example, 1-75 mg, preferably, 10-40 mg, more preferably, 10 mg, 20 mg, or 40 mg.

The daily dose of siponimod for an adult is, for example, 0.25 mg-10 mg, preferably, 0.25 mg, 0.5 mg, 1.25 mg, 2 mg, or 10 mg, for example, as siponimod fumarate.

The daily administration frequency of the therapeutic agent of the present invention can be appropriately increased or decreased according to various conditions such as the kind of the disease to be the treatment target, progression of disease or degree of symptoms, age and body weight of patients, and the like. The frequency is generally, for example, once per day, twice per day, three times per day, preferably once per day, for an adult.

The therapeutic agent for myalgic encephalomyelitis/chronic fatigue syndrome (ME/CFS) of the present invention contains the active ingredient, and can further used in combination with or formulated as a combination agent with known therapeutic agents for myalgic encephalomyelitis/chronic fatigue syndrome (ME/CFS). Examples of the known therapeutic drug for myalgic encephadomyelitis/chronic fatigue syndrome (ME/CFS) include pregabalin, mirogabalin, tramadol, acetaminophen, non-steroidal anti-inflammatory agents (NSAIDs) (e.g., aspirin, loxoprofen, ibuprofen, celecoxib and the like), monoamine oxidase (MAO) inhibitor (e.g., selegiline, rasagiline, safinamide, isoniazid, and the like), serotonin selective reuptake inhibitor (SSRI) (e.g., fluvoxamine, paroxetine, sertraline, escitalopram, and the like), serotonin/noradrenaline selective reuptake inhibitor (SNRI) (e.g., milnacipran, duloxetine, and the like), noradrenergic and specific serotonergic antidepressant (NaSSA) (e.g., mirtazapine and the like), benzodiazepine sleeping drugs (e.g., etizolam and the like), nonbenzodiazepine sleeping drugs (e.g., zolpidem, zopiclone, and the like), clomipramine, an extract from inflamed cutaneous tissue of rabbits inoculated with vaccinia virus (e.g., Neurotropin and the like), Chinese herbal medicament (e.g., Hochuekkito, Juzentaihoto, and the like), Ampligen (registered trademark), and the like.

EXAMPLE

The present invention is explained in more detail in the following by referring to Examples, which are not to be construed as limitative.

Example 1

Effectiveness in Myalgic Encephalomyelitis/Chronic Fatigue Syndrome (ME/CFS) Animal Model A myalgic encephalomyelitis/chronic fatigue syndrome (ME/CFS)-improving effect by the administration of the compound (amiselimod hydrochloride) relating to the present invention was verified as follows according to the method of Tanaka et al. (Establishment and assessment of a rat model fatigue. Neuroscience letters 2003, 352: 159-162) using a water-immersion stress loaded rat (fatigue rat) model.

The animal used was 9-week-old Slc:SD rat. The rats were bred (water-immersion breeding) for 6 days in a plastic cage (W: 445×D: 276×H: 204 mm) containing tap water (water temperature: 23±1° C.) to a height of 1.5 cm, and a weight-loaded forced swimming test was conducted on the final day. In the weight-loaded forced swimming test, a rat with a weight equivalent to 8% of its body weight attached to its tail was placed in a circular water tank (diameter: 18 cm, height: 70 cm, water depth: 40 cm, water temperature: 23±1° C.), and the time from the start of swimming until the rat's nose sinks from the water surface for 20 seconds was measured. The weight-loaded forced swimming test was conducted blindly.

Amiselimod hydrochloride (0.1, 0.3 and 1 mg/kg administration) was orally administered once a day for 6 days from the start date of the water-immersion breeding. As control groups, a normal control group for normal breeding and a fatigue control group for water-immersion breeding were set, and the vehicle (0.5% HPMC) was administered to both groups. The number of cases was 10 in each group.

As a result, the swimming time of the fatigue control group was significantly shorter than that of the normal control group. Administration of 0.1, 0.3 and 1 mg/kg amiselimod hydrochloride significantly prolonged the swimming time as compared to the fatigue control group (FIG. 1).

Example 2

Method of Generating Fibromyalgia (FM) Model and Evaluation Method Thereof

FM is a chronic intractable disease whose main symptom is systemic pain. It has been reported that it occurs very frequently with ME/CFS, and there are many common aspects such as similar symptoms, activation of microglia in the spinal cord and brain, and the like (Fibromyalgia Medical Guideline 2017 Japan College of Fibromyalgia Investigation).

As non-clinical FM models, plural models due to (1) stress load, (2) drug administration, (3) nerve damage, and the like have been reported. As an example of (1), various physical and mental stress loads including forced swimming stress (Suarez-Roca, H., Quintero, L., Arcaya, J. L., Maixner, W., Rao, S. G., Stress-induced muscle and cutaneous hyperalgesia: differential effect of milnacipran, Physiol. Behav., 88 (2006) 82-87), chronic restraint stress (Bardin, L., Malfetes, N., Newman-Tancredi, A., Depoortère, R., Chronic restraint stress induces mechanical and cold allodynia, and enhances inflammatory pain in rat: Relevance to human stress-associated painful pathologies, Behav. Brain Res., 205 (2009) 360-366), repeated cold stress (Nasu, T., Taguchi, T., Mizumura, K., Persistent deep mechanical hyperalgesia induced by repeated cold stress in rats, Eur. J. Pain, 14 (2010) 236-244; and Nishiyori, M., Ueda, H., Prolonged gabapentin analgesia in an experimental mouse model of fibromyalgia, Mol. Pain, 4 (2008) 52), multiple continuous stress (Yasui, M., Yoshimura, T., Takeuchi, S., Tokizane, K., Tsuda, M., Inoue, K., Kiyama, H., A Chronic fatigue syndrome model demonstrates mechanical allodynia and muscular hyperalgesia via spinal microglial activation, Glia, 62 (2014) 1407-1417), sound stress (Khasar, S. G., Dina, O. A., Green, P. G., Levine, J. D., Sound stress-induced long-term enhancement of mechanical hyperalgesia in rats is maintained by sympathoadrenal catecholamines, J. Pain, 10 (2009) 1073-1077), maternal separation stress (Green, P. G., Chen, X., Alvarez, P., Ferrari, L. F., Levine, J. D., Early-life stress produces muscle hyperalgesia and nociceptor sensitization in the adult rat, Pain, 152 (2011) 2549-2556), and the like are used. The example of (2) is generated by subcutaneous administration of a biogenic amine depleting agent, reserpine, or administration of acidic saline (pH 4) to gastrocnemial muscle. As an example of (3), a phenotype has been reported in which the subdiaphragmatic vagus nerve is cut and the pain threshold is lowered in any of these methods.

A method of generating an FM model by administration of reserpine, which is widely used among the above, and an evaluation method thereof are described. Reserpine is prepared to have a final concentration of 0.5% acetic acid, and is administered subcutaneously to the back of SD rats at a dose of 1 mg/kg once a day for 3 days. To evaluate the pain threshold for mechanical stimulation, the von Frey test or the like is performed, in which von Frey filament is pressed perpendicularly to the sole of paw and the threshold is measured when the paw is raised. To evaluate the pain threshold for pressure stimulation, a Randall Selitto method or the like is performed in which a pressure that increases continuously at a constant rate is applied to the hind limb of rat and the escape threshold is measured. Amiselimod hydrochloride is prepared in a vehicle such as 0.5% HPMC, and is orally administered at the same time as reserpine administration or 5 days after the final administration of reserpine, and the prophylactic effect and therapeutic effect on a decrease in the pain threshold are confirmed by the above-mentioned evaluation.

INDUSTRIAL APPLICABILITY

The therapeutic agent of the present invention containing 2-amino-2-[2-(4-heptyloxy-3-trifluoromethylphenyl)ethyl] propane-1,3-diol or a pharmaceutically acceptable salt thereof, and the like is useful as a therapeutic agent for myalgic encephalomyelitis/chronic fatigue syndrome (ME/CFS) and the like.

This application is based on patent application No. 2020-019153 filed in Japan, the contents of which are encompassed in full herein.

The invention claimed is:

1. A method for treating a disease selected from myalgic encephalomyelitis/chronic fatigue syndrome, and fibromyalgia, comprising administering to a patient suffering from myalgic encephalomyelitis/chronic fatigue syndrome or fibromyalgia an effective amount of 2-amino-2-[2-(4-heptyloxy-3-trifluoromethylphenyl)ethyl]propane-1,3-diol or a pharmaceutically acceptable salt thereof.

2. The method according to claim 1, wherein the disease that the patient is suffering from is myalgic encephalomyelitis/chronic fatigue syndrome.

3. The method according to claim 2, wherein the myalgic encephalomyelitis/chronic fatigue syndrome is myalgic encephalomyelitis/chronic fatigue syndrome associated with fatigue symptoms.

4. The method according to claim 1, wherein the myalgic encephalomyelitis/chronic fatigue syndrome is myalgic encephalomyelitis/chronic fatigue syndrome associated with fatigue symptoms.

5. The method according to claim 1, wherein administering the 2-amino-2-[2-(4-heptyloxy-3-trifluoromethylphenyl)ethyl]propane-1,3-diol or pharmaceutically acceptable salt thereof is at a daily dose ranging from 0.05 mg to 1.0 mg.

6. The method according to claim 1, wherein the 2-amino-2-[2-(4-heptyloxy-3-trifluoromethylphenyl)ethyl]propane-1,3-diol or pharmaceutically acceptable salt thereof is administered once per day, twice per day or three times per day.

7. The method according to claim 1, wherein the 2-amino-2-[2-(4-heptyloxy-3-trifluoromethylphenyl)ethyl]propane-1,3-diol or pharmaceutically acceptable salt thereof is administered in a composition, and the composition comprises a pharmaceutically acceptable additive.

8. The method according to claim 1, wherein the 2-amino-2-[2-(4-heptyloxy-3-trifluoromethylphenyl)ethyl]propane-1,3-diol or pharmaceutically acceptable salt thereof is administered with an additional therapeutic agent.

9. A method for relieving fatigue symptoms, the method comprising:

administering an effective amount of 2-amino-2-[2-(4-heptyloxy-3-trifluoromethylphenyl)ethyl]propane-1,3-diol or a pharmaceutically acceptable salt thereof to a subject, wherein the subject suffers from myalgic encephalomyelitis or chronic fatigue syndrome.

10. The method according to claim 9, wherein administering the 2-amino-2-[2-(4-heptyloxy-3-trifluoromethylphenyl)ethyl]propane-1,3-diol or pharmaceutically acceptable salt thereof is at a daily dose ranging from 0.05 mg to 1.0 mg.

11. The method according to claim 9, wherein the 2-amino-2-[2-(4-heptyloxy-3-trifluoromethylphenyl)ethyl]propane-1,3-diol or pharmaceutically acceptable salt thereof is administered once per day, twice per day or three times per day.

12. The method according to claim 9, wherein the 2-amino-2-[2-(4-heptyloxy-3-trifluoromethylphenyl)ethyl]propane-1,3-diol or pharmaceutically acceptable salt thereof is administered in a composition, and the composition comprises a pharmaceutically acceptable additive.

13. The method according to claim 9, wherein the 2-amino-2-[2-(4-heptyloxy-3-trifluoromethylphenyl)ethyl]propane-1,3-diol or pharmaceutically acceptable salt thereof is administered with an additional therapeutic agent.

* * * * *